(12) United States Patent
Latil et al.

(10) Patent No.: US 7,875,657 B2
(45) Date of Patent: Jan. 25, 2011

(54) TRANS-1,2 DICHLOROETHYLENE COMPOSITION

(75) Inventors: Laurent Latil, Moidieu de Tourbes (FR); Vincent Enaux, Bessenay (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/616,456

(22) Filed: Nov. 11, 2009

(65) Prior Publication Data

US 2010/0056658 A1   Mar. 4, 2010

Related U.S. Application Data

(63) Continuation of application No. 11/814,816, filed on Jul. 26, 2007, now abandoned.

(30) Foreign Application Priority Data

Feb. 23, 2005   (FR)   .................................. 05 01832
Feb. 3, 2006   (WO)   ................ PCT/FR2006/000252

(51) Int. Cl.
  *C08J 9/14*   (2006.01)

(52) U.S. Cl. .......................... 521/131; 252/67; 252/364; 510/407; 510/408; 510/412; 510/415; 516/8; 521/170; 521/181

(58) Field of Classification Search ................. 521/131, 521/170, 181; 510/407, 408, 412, 415; 252/67, 252/364; 516/8
See application file for complete search history.

(56) References Cited

U.S. PATENT DOCUMENTS

| | | |
|---|---|---|
| 3,349,039 A | 10/1967 | Renault et al. |
| 6,110,229 A | 8/2000 | Swan et al. |
| 6,635,686 B2 | 10/2003 | Bogdan et al. |
| 6,764,990 B1 | 7/2004 | Bogdan et al. |
| 6,790,820 B2 | 9/2004 | Bogdan et al. |
| 7,144,926 B2 | 12/2006 | Galaton et al. |
| 2003/0050356 A1 | 3/2003 | Bogdan et al. |

*Primary Examiner*—John Cooney
(74) *Attorney, Agent, or Firm*—Steven D. Boyd

(57) ABSTRACT

The present invention relates to a composition based on trans-1,2-dichloroethylene. A subject-matter of the invention is more particularly a nonflammable composition comprising trans-1,2-dichloroethylene and at least two hydrofluorocarbons and its uses.

8 Claims, No Drawings

TRANS-1,2 DICHLOROETHYLENE COMPOSITION

The present application is a continuation of U.S. patent application Ser. No. 11/814,816 filed Jul. 26, 2007.

FIELD OF THE INVENTION

The present invention relates to a composition based on trans-1,2-dichloroethylene. A subject-matter of the invention is more particularly a nonflammable composition comprising trans-1,2-dichloroethylene and at least two hydrofluorocarbons and its uses.

BACKGROUND OF THE INVENTION trans-1,2-Dichloroethylene is a chlorinated solvent which has a boiling point of 48° C. and which, in the same way as trichloroethane, trichloroethylene and perchloroethylene, has a good solubilizing power, in particular for fatty substances (lubricants, oils, greases). Its use has to date been relatively limited because of the existence, for this solvent, of a flash point. trans-1,2-Dichloroethylene effectively has a flash point of between −11° C. and −4° C. under the standard determination conditions (Standard D3828-02: closed cup, Setaflash).

U.S. Pat. No. 3,349,039 discloses compositions based on trans-1,2-dichloroethylene and on 1,1,2-trifluoro-1,2,2-trichloroethane or on methylene chloride, the latter two compounds making it possible to suppress the flash point of trans-1,2-dichloroethylene. However, these mixtures are not really of interest now as 1,1,2-trifluoro-1,2,2-trichloroethane has been banned since the Montreal protocol and methylene chloride is strictly regulated (harmful Carcinogenic, Mutagenic and Reprotoxic substance).

U.S. Pat. No. 6,100,229 discloses compositions based on azeotropic trans-1,2-dichloroethylene and 1,1,1,3,3-pentafluoropropane mixtures but with a high content of 1,1,1,3,3-pentafluoropropane. The disadvantage of such a mixture is its relatively low boiling point, a value in the region of 20° C. for a composition comprising only 20% of trans-1,2-dichloroethylene.

Furthermore, the use of trans-1,2-dichloroethylene with a blowing agent in the manufacture of thermosetting polymer foams is known.

In many applications, the components of the polyurethane foams are premixes. More generally, the formulation of the foams is premixed as two components. The first component, better known under the name "component A", comprises the isocyanate or polyisocyanate composition. The second component, better known under the name "component B", comprises the polyol or the mixture of polyols, the surface-active agent, the catalyst or catalysts and the blowing agent or agents.

The "component B" presents problems of flammability, even when the blowing agent forming part of the composition of the premix is nonflammable.

In addition, problems of rise in pressure in the containers holding the "component B" are often encountered during their storage.

DETAILED DESCRIPTION OF THE INVENTION

The present invention thus provides compositions which make it possible to solve, in all or in part, the abovementioned problems.

A first subject-matter of the present invention is thus a composition comprising trans-1,2-dichloroethylene, 1,1,1,3,3-pentafluoropropane and 1,1,1,2-tetrafluoroethane (134a).

The composition according to the invention preferably comprises from 10 to 98% by weight of trans-1,2-dichloroethylene, from 1 to 89% by weight of 1,1,1,3,3-pentafluoropropane and from 1 to 80% by weight of 1,1,1,2-tetrafluoroethane (134a).

Advantageously, the composition according to the invention comprises from 25 to 95% by weight of trans-1,2-dichloroethylene, from 1 to 45% by weight of 1,1,1,3,3-pentafluoropropane and from 1 to 30% by weight of 1,1,1,2-tetrafluoroethane (134a).

The composition according to the invention comprising from 45 to 95% by weight of trans-1,2-dichloroethylene, from 1 to 45% by weight of 1,1,1,3,3-pentafluoropropane and from 1 to 30% by weight of 1,1,1,2-tetrafluoroethane (134a) is advantageously preferred.

A composition comprising from 80 to 95% by weight of trans-1,2-dichloroethylene, from 1 to 19% by weight of 1,1,1,3,3-pentafluoropropane and from 1 to 15% by weight of 1,1,1,2-tetrafluoroethane (134a) is particularly preferred.

The composition according to the invention can additionally comprise a polyol or a mixture of polyols.

A second subject-matter of the present invention is thus a composition comprising a polyol or a mixture of polyols and the ternary mixture of trans-1,2-dichloroethylene, of 1,1,1,3,3-pentafluoropropane and of 1,1,1,2-tetrafluoroethane (134a) of the first subject-matter.

The ternary mixture of the first subject-matter preferably represents between 1 and 60 parts by weight per 100 parts by weight of polyol or mixture of polyols in the composition of the second subject-matter. Advantageously, it represents between 5 and 35 parts by weight per 100 parts by weight of polyol or mixture of polyols.

Mention may in particular be made, as polyols, of glycerol, ethylene glycol, trimethylolpropane, pentaerythritol, polyether polyols, for example those obtained by condensation of an alkylene oxide or of a mixture of alkylene oxides with glycerol, ethylene glycol, trimethylolpropane or pentaerythritol, or polyester polyols, for example those obtained from polycarboxylic acids, in particular oxalic acid, malonic acid, succinic acid, adipic acid, maleic acid, fumaric acid, isophthalic acid or terephthalic acid, with glycerol, ethylene glycol, trimethylolpropane or pentaerythritol.

The polyether polyols obtained by addition of alkylene oxides, in particular ethylene oxide and/or propylene oxide, to aromatic amines, in particular the mixture of 2,4- and 2,6-toluenediamine, are also suitable.

Another subject-matter of the present invention is a process for the manufacture of polyurethane foams. This process consists in reacting an organic polyisocyanate (including the diisocyanate) with the composition according to the second subject-matter. This reaction can be activated using an amine and/or other catalysts and surface-active agents.

Mention may in particular be made, as polyisocyanate, of aliphatic polyisocyanates with a hydrocarbon group which can range up to 18 carbon atoms, cycloaliphatic polyisocyanates with a hydrocarbon group which can range up to 15 carbon atoms, aromatic polyisocyanates with an aromatic hydrocarbon group having from 6 to 15 carbon atoms and arylaliphatic polyisocyanates with an arylaliphatic hydrocarbon group having from 8 to 15 carbon atoms.

The preferred polyisocyanates are 2,4- and 2,6-diisocyanatotoluene, diphenylmethane diisocyanate, polymethylenepolyphenyl isocyanate and their mixture. Modified polyisocyanates, such as those comprising carbodiimide groups, urethane groups, isocyanurate groups, urea groups or biurea groups, may also be suitable.

The composition according to the first subject-matter can be used as solvent. The various applications are in particular the treatment of solid surfaces, such as, for example, the cleaning, degreasing or drying of solid surfaces and the defluxing of printed circuits, the dry-cleaning of textiles or the cleaning of refrigerating plants.

The composition according to the first subject-matter can also be used as blowing agent for thermosetting polymer foams, for example phenol/formaldehyde condensates or polyurethane. It is very particularly suitable for the manufacture of polyurethane foams.

The composition according to the first subject-matter can also be used as heat-exchange fluids, agents for depositing silicones and/or aerosol propellants.

EXPERIMENTAL PART

Example 1

A composition is prepared composed of 100 g of a Stepanpol PS2412 polyol (polyester type) and of 7 g of a mixture containing 82% by weight of trans-1,2-dichloroethylene, 15% by weight of 1,1,1,3,3-pentafluoropropane and 3% by weight of 1,1,1,2-tetrafluoroethane (134a). This composition does not exhibit a flash point, even at 80° C., under the standard determination conditions with the Setaflash test, Standard D3828-02.

Example 2

A composition is prepared composed of 100 g of a Stepanpol PS2412 polyol (polyester type) and of 7 g of a mixture containing 85% by weight of trans-1,2-dichloroethylene, 10% by weight of 1,1,1,3,3-pentafluoropropane and 5% by weight of 1,1,1,2-tetrafluoroethane (134a). This composition does not exhibit a flash point, even at 80° C., under the standard determination conditions with the Setaflash test, Standard D3828-02.

The invention claimed is:

1. A method of forming a thermosetting foam comprising reacting a thermosetting polymer foam forming material in the presence of a blowing agent composition comprising from 45 to 95% by weight of trans-1,2-dichloroethylene, from 1 to 45% by weight 1,1,1,3,3-pentafluoropropane and from 1 to 30% by weight of 1,1,1,2-tetrafluoroethane (134a) with said % by weights being based on the total weight of the blowing agent composition.

2. The method of claim 1 wherein said thermosetting foam material is selected from the group consisting of, phenol/formaldehyde condensate and polyurethane.

3. The method of claim 1 further comprising adding an activator selected from the group consisting of amines, catalyst and surface active agents.

4. The method of claim 2 wherein said polyurethane is formed by reacting a polyol and an aliphatic polyisocyanate having a hydrocarbon group comprising up to about 18 carbon atoms.

5. The method of claim 2 wherein said polyurethane is formed by reacting a polyol and a cycloaliphatic polyisocyanate having a hydrocarbon group comprising up to about 15 carbon atoms.

6. The method of claim 2 wherein said polyurethane is formed by reacting a polyol and an aromatic polyisocyanate having a hydrocarbon group comprising from about 6 to about 15 carbon atoms.

7. The method of claim 2 wherein said polyurethane is formed by reacting a polyol and a arylaliphatic polyisocyanate having a arylaliphatic hydrocarbon group comprising from about 8 to about to about 15 carbon atoms.

8. The method of claim 2 wherein said polyurethane is formed by reacting a polyol and a polyisocyanate selected from the group consisting of 2,4-diisocyanatotoluene, 2,6-diisocyanatotoluene, diphenylmethane diisocyanate, polymethylenepolyphenyl isocyanate and mixtures thereof.

* * * * *